United States Patent [19]

Jones

[11] Patent Number: 4,795,342

[45] Date of Patent: Jan. 3, 1989

[54] CALIBRATED SPRING MODULE

[76] Inventor: Marston Jones, Rainbow Farm, Rte. 1, Box 115C, Salisbury, Md. 21801

[21] Appl. No.: 832,240

[22] Filed: Feb. 24, 1986

Related U.S. Application Data

[63] Continuation-in-part of Ser. No. 597,602, Apr. 6, 1984, abandoned, which is a continuation-in-part of Ser. No. 439,213, Nov. 4, 1982, Pat. No. 4,462,800.

[51] Int. Cl.$^4$ .............................................. A61C 3/00
[52] U.S. Cl. ....................................... 433/19; 433/22
[58] Field of Search ........................ 433/19, 22, 18, 21, 433/12, 13, 5, 7

[56] References Cited

U.S. PATENT DOCUMENTS

| | | | |
|---|---|---|---|
| 360,695 | 4/1987 | Holmes | 433/7 |
| 473,040 | 4/1892 | Wilder | 433/18 |
| 2,959,856 | 11/1960 | Gurin | 433/22 |
| 3,238,619 | 3/1966 | Brunson et al. | 433/13 |
| 3,508,332 | 4/1970 | Armstrong | 433/22 |
| 3,618,214 | 11/1971 | Armstrong | 433/19 |
| 3,798,773 | 3/1974 | Northcutt | 433/19 |
| 3,964,165 | 6/1976 | Stahl | 433/15 |
| 4,259,065 | 3/1981 | DeWoskin | 433/5 |
| 4,462,800 | 7/1984 | Jones | 433/22 |

FOREIGN PATENT DOCUMENTS

| | | | |
|---|---|---|---|
| 374163 | 4/1923 | Fed. Rep. of Germany | 433/19 |
| 1252156 | 12/1960 | France | 433/19 |

Primary Examiner—John J. Wilson
Attorney, Agent, or Firm—Nies, Webner, Kurz & Bergert

[57] ABSTRACT

An orthodontic device for use in applying a constant calibrated force to certain teeth or groups of teeth so as to cause the teeth to change position within the mouth over a period of time. The device includes a spring module having a telescope mechanism with inner plunger portion and outer tube portion, and with a calibrated compression coil spring concentrically positioned on the inner plunger portion within the tube portion. The telescope plunger is of a bent arm configuration to assist in providing clearance relative to other installed orthodontic means. A notch is provided in the forward inner wall of the telescope tube to assist in controlling operation of the spring. A bifurcated yoke on the plunger end and a ball and socket type anchor pin on the tube end are employed to secure the device to brace wires mounted on the teeth of a patient. A flat plate is attached to the inner end of the anchor pin to exert force against adjacent teeth and thus counteract the tendency of the spring to rotate about its longitudinal axis.

11 Claims, 3 Drawing Sheets

FIG. 3
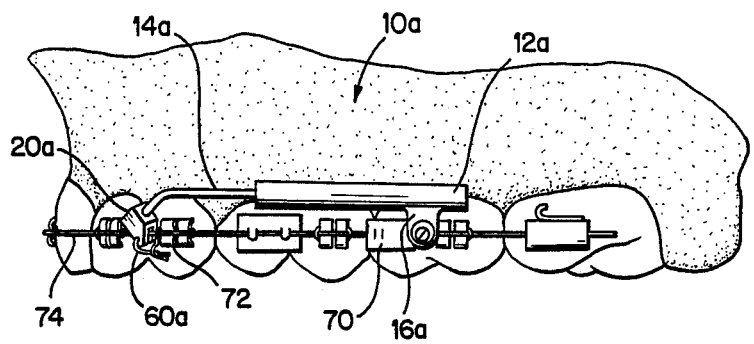
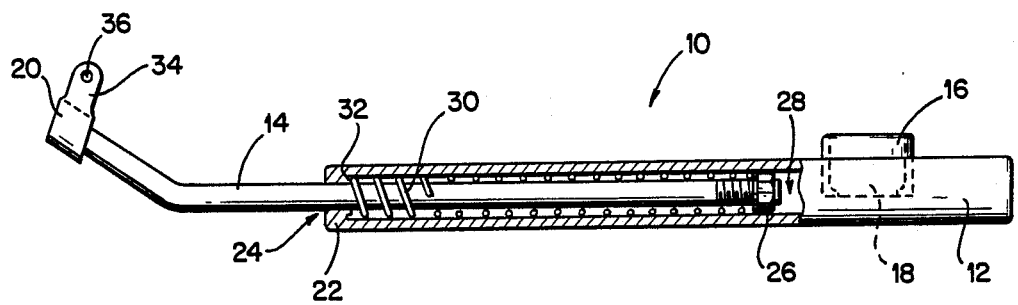
FIG. 4
FIG. 5
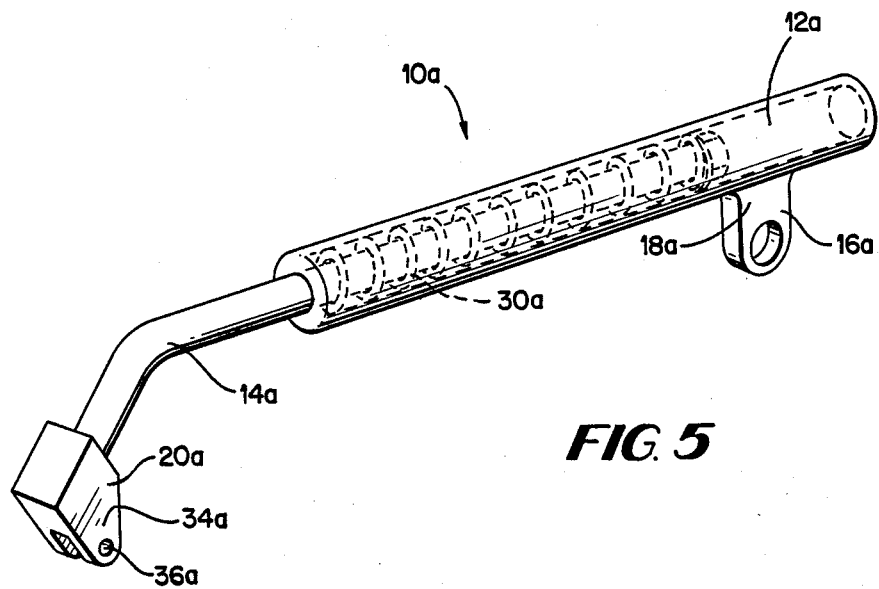

CALIBRATED SPRING MODULE

This is a continuation-in-part of application Ser. No. 597,602 filed Apr. 6, 1984, now abandoned, which is a continuation-in-part of application Ser. No. 439,213 filed Nov. 4, 1982, now U.S. Pat. No. 4,462,800.

BACKGROUND AND SUMMARY OF THE INVENTION

The present invention relates to an orthodontic device for use in repositioning teeth within the mouth of a patient. More particularly, the present invention is concerned with an orthodontic device which may be attached to orthodontic brace wires connected to teeth of the upper and lower jaw, or between teeth of the same jaw, for the purpose of applying a constant calibrated force to the teeth so as to cause the teeth to change position within the mouth over a period of time.

Previous spring operated devices for use in moving teeth within the mouth of a patient have included the devices described in the following Holmes U.S. Pat. Nos. 360,695 ; 3,618,214 to Armstrong; 3,798,773 to Northcutt; and 4,259,065 to DeWoskin.

The Holmes patent discloses a spring regulating appliance which is attached between a tooth and a securing position on a temporary plate applied to the palate or roof of the mouth. The Armstrong patent discloses the use of plurality of coiled springs which are telescoped together and secured to a pair of eyelets for engagement with hooks on orthodontic arch wires. The Northcutt patent discloses a compression device for use in realignment of the teeth which includes a pair of ring and telescopic tube arrangements which in one embodiment may be attached directly to the brace wires on the upper and lower jaw. The DeWoskin patent discloses traction apparatus having a pair of side members to be worn on opposite sides of the patient's head. Each side member has a tensioning assembly which includes a spring mounted within a tube.

Devices for locking various appliances on a brace or arch wire include that described in U.S. Pat. No. 3,238,619 to Brunson et al. wherein an arch wire locking device for an orthodontic bracket affixed to a tooth band is disclosed in which the arch wire is retained within a slot in the casing of the bracket.

It is an object of the present invention to provide an improved orthodontic device which may be attached directly to the orthodontic brace wires on the upper and lower jaw, or between teeth of the same jaw, for use in repositioning teeth.

It is an additional object of the invention to provide an orthodontic device which is of compact construction for use in moving teeth within the mouth of a patient.

It is a further object of the invention to provide an orthodontic device which is constructed so as to be comfortable in the mouth of a patient and to eliminate various discomforting features of prior art devices.

It is an additional object of the present invention to provide an orthodontic device which remains installed and activated throughout each 24 hour day and functions to reposition the teeth, while not interfering with chewing or other normal functions of the mouth.

It is another object of the invention to provide continual application of previously determined corrective forces for the purpose of changing the position of one or more teeth within the mouth of a patient.

It is a further object of the invention to provide an orthodontic device which is of relatively simple construction, thus facilitating installation and use of the device in the mouth of a patient.

The foregoing as well as additional objects are obtained by the orthodontic device of the present invention in the form of a calibrated spring module which is particularly well suited for the purpose of moving teeth with a constant calibrated force. The spring module device includes a telescope mechanism having inner plunger portion and outer tube portion, and with resilient means which may be in the form of a calibrated compression coil spring concentrically positioned on the inner telescope plunger portion within the telescope outer tube portion. The spring is longitudinally retained between a notched end wall of the telescope tube and a flange on the inner end of the telescope plunger portion such that, in the operative position, the telescoped members are spring biased so as to be urged to a retracted condition.

In one embodiment, the telescope mechanism is attached to brace wires located on teeth of the upper and lower jaw or on teeth of the same jaw by the use of a ball and socket mechanism at one end of the device and a birfurcated yoke at the opposite end. The ball and socket mechanism, which is attached to the tube portion of the telescope mechanism, is provided with an anchor pin or trunnion member extending inwardly of the socket and a flat plate member attached to the inner end of the anchor pin and extending generally perpendicular to the longitudinal axis of the anchor pin. A radial slot is provided between the anchor pin and the plate member for receiving an arch or brace wire. A screw member extends through the anchor pin to retain the arch wire in the slot.

At the opposite end of the device, the bifurcated yoke is attached to the outer end of the plunger portion of the telescope mechanism. The yoke has a pair of lug portions adapted to receive between them an arch wire. A tie wire extends through respective bores in the lugs to effectively enclose the arch wire between the lugs and the tie wire.

In using the spring module, the attachment members at either end of the device are secured to orthodontic means and fixed in the desired location on the teeth. Upon attachment of the yoke and the ball and socket member in position so that the spring is compressed, the device is then in an activated condition for use in moving teeth with a constant calibrated force. The spring may be calibrated to return to its original dimension with a specific force such as approximately four to six ounces.

The characteristic features of the present invention include the feature whereby an enclosed coiled spring is installed in a compressed condition within a telescope mechanism and positioned between teeth either of the same jaw or of the upper and lower jaw in such a manner that spring bias force tends to pull teeth toward each other. An additional feature of the present invention resides in the baised unit having a ball and socket member attached to the tube portion of a telescope mechanism, and with a bifurcated yoke attached to the outer end of the plunger portion of the telescope mechanism, wherein the plunger rod is bent to form an angle which effectively prevents the device from contacting orthogontic means previously installed in the mouth of a patient, while allowing freedom of movement of the telescope mechanism during use within the mouth of the patient.

A primary feature of the invention is the use of a compressed coiled spring extending axially within the telescoped member with the spring being calibrated to exert a known force on one or more teeth as it seeks to expand to its original dimension. The present invention has been found to be particularly effective in repositioning the canine and cuspid teeth as well as the six front teeth of either jaw as a group.

BRIEF DESCRIPTION OF THE DRAWINGS

FIG. 3 is a perspective side view showing a second embodiment of the present invention as installed on the upper jaw of a patient.

FIG. 4 is a top plan view in partial cross-section of the orthodontic device shown in FIGS. 1 and 2.

FIG. 5 is a perspective view of the orthodontic device shown in FIG. 3.

DESCRIPTION OF THE PREFERRED EMBODIMENTS

Figures 1, 2:
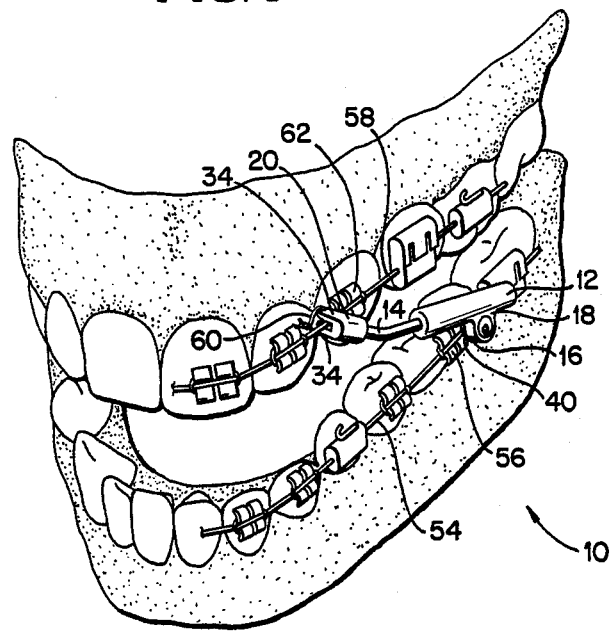
FIG. 1 is a perspective view from the front of the mouth showing one embodiment of the orthodontic device of the present invention as installed in the mouth of a patient.
FIG. 2 is a perspective view showing the device of FIG. 1 in a modified installation on the jaws of a patient.

In the embodiments of the invention as shown in FIGS. 1–10, there is provided an orthodontic device 10 in the form of a spring module having telescoping members which include outer tube portion 12 and inner plunger portion 14. The tube portion 12 is provided with a socket 16 connected to the tube 12 adjacent the outer end thereof by an arm 18 which extends substantially perpendicular to the tube 12. The plunger portion 14 is provided with a bifurcated yoke 20 attached at the outer end of the plunger 14.

Figure 6:
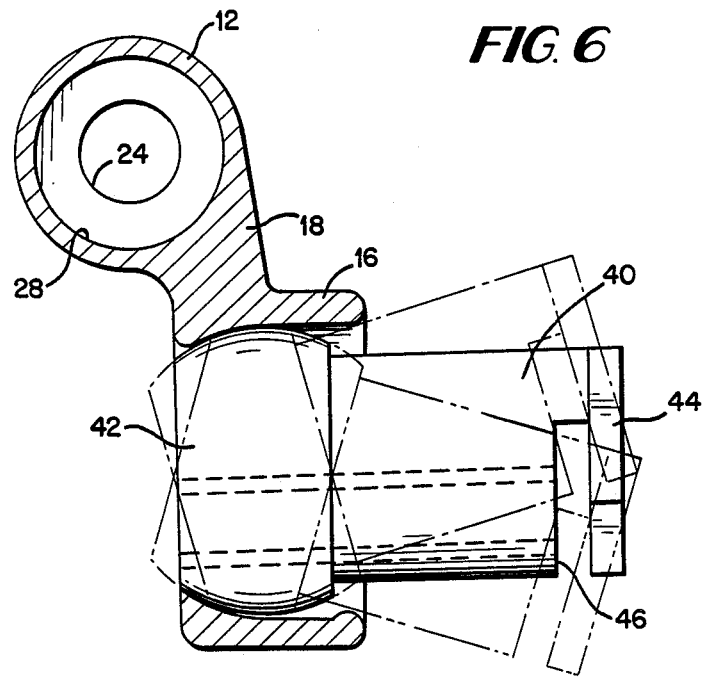
FIG. 6 is an enlarged cross-sectional view of the orthodontic device of the present invention, showing the anchor pin or trunnion member mounted in the socket portion of the device.

The tube 12 may be formed from a suitable metal or plastic material such as stainless steel. The socket 16 and arm 18 may be manufactured separately as a single piece, also from a material such as stainless steel, with the arm 18 then being welded to the tube 12 at a suitable position to provide the desired configuration. Generally, the socket 16 and arm 18 will be positioned in proximity to the outer end of the tube 12 opposite to the end from which the plunger 14 projects. The socket 16 is formed in a plane perpendicular to the axis of the socket 16, which plane extends generally tangentially to the tube 12, as shown in FIG. 6.

The plunger 14 and yoke 20 will also be formed of a suitable metal or plastic material such as stainless steel. The plunger 14 and the yoke 20 may be formed separately and then welded together or, in some instances, formed as an integral unit.

The telescope tube 12 is provided with an end wall 22 at the opposite end from socket member 16. the end wall 22 has a central opening 24 therein which receives the plunger 14 and allows the plunger 14 to move longitudinally in sliding engagement with the surfaces of the end wall 22 surrounding the opening 24. The telescope plunger 14 is provided with a retaining flange 26 at the opposite end from the yoke 20. The flange 26 extends radially outwardly from the plunger 14 so as to fit in sliding engagement with the inner wall of the tube 12. The bore 28 within tube 12 extends throughout the length of the tube 12, thus allowing longitudinal movement of the plunger 14 within substantially the entire length of the tube 12.

Figure 9:
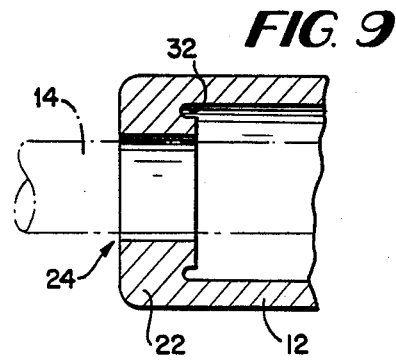
FIG. 9 is an enlarged partial elevation in cross-section of the telescope tube portion of the present invention.

A coil spring 30 is concentrically positioned on the plunger 14 and within the telescope tube 12. Thus as shown in FIG. 4, the spring 30 is longitudinally retained between the end wall 22 of the telescope tube 12 and the flange 26 of the telescope plunger 14, with the result that the telescope members 12, 14 may be spring biased to a retracted condition when installed in the mouth of a patient. A notch 32 is provided around the inner surface of the end wall 22 of tube 12, adjacent the intersection of the end wall 22 with the inner surface of the side walls of the tube 12, as shown in FIGS. 4 and 9, for the purpose of receiving the forward end portion of the spring 30. The notch 32, in the shape of a circular channel, should have a diameter equal to or slightly greater than that of the spring 30. A similar construction is provided for the embodiment of FIG. 5.

In the embodiment as shown in FIGS. 1, 2 and 4, the plunger 14 is bent so that the outer arm of the plunger 14 forms an angle of approximately 45 degrees relative to the remainder of the plunger 14. The remainder of the plunger 14 is of a straight configuration which is at least equal to the length of the tube 12. The yoke 20 includes a pair of lug portions 34 adapted to receive between them an arch wire of orthodontic means affixed to the teeth of a patient. The lugs 34 form an angle of greater than 90 degrees with the outer end of the plunger 14. Such angle may be about 110 to 120 degrees, for example. Each lug 34 is provided with a bore 36 for receiving a tie wire 60 which acts to enclose the arch wire. The bent plunger 14 lies in the same plane which symmetrically bisects the yoke 20 equidistant from the lugs 34. As shown in FIGS. 1 and 2, this embodiment is employed by attaching the device 10 between the upper and lower jaw.

In the embodiment as shown in FIGS. 3 and 5, the lugs 34a of the yoke 20a form an angle of approximately 90 degrees with the outer end of the plunger 14a. Also, the outer arm of the plunger 14a is bent at a greater angle than in the case of the previous embodiment, so that the outer arm of the plunger 14a forms an angle of approximately 60 degrees relative to an extension of the remainder of the plunger 14a. As shown in FIG. 3, this embodiment is employed by attaching the ends of the device 10a to respective brace wire locations with both of such locations being on a single jaw, i.e, on either the upper or lower jaw. The device 10a should be installed so that the telescoping members 12a, 14a are positioned generally above the brace wire when installed on the upper jaw, while such members 12a, 14a will be positioned generally below the brace wire when installed on the lower jaw. In either case the telescoping members 12a, 14a will remain clear of the gums of the patient.

Figure 7:
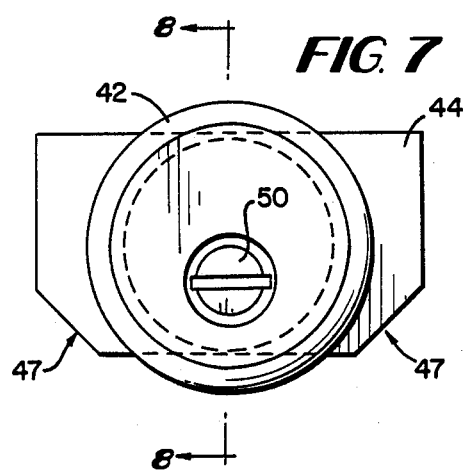
FIG. 7 is an outer end view of the anchor pin member of FIG. 6.
Figure 8:
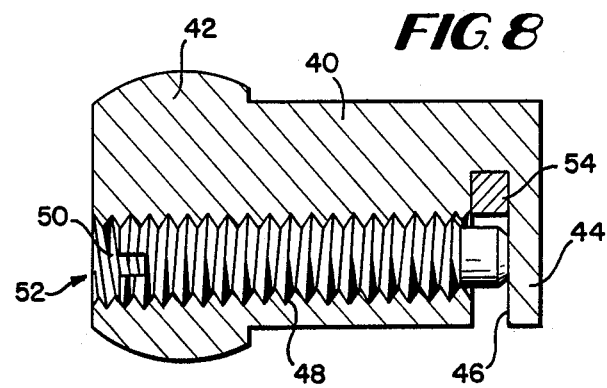
FIG. 8 is a cross-sectional elevation of the pin member of FIG. 7 taken along line 8—8 of FIG. 7.

The ball and socket mechanism employed with the present invention is shown in detail in FIGS. 6 through 8. As shown therein, an anchor pin or trunnion member 40 is provided with a ball shaped outer end portion 42 which is rotatably mounted in and retained by the socket 16. The anchor pin 40 should be capable of rotation, both vertically and laterally, by an angle such as about 20 degrees on each side of the longitudinal axis, or a total of about 40 degrees of maneuverability, thus allowing for movement of the anchor pin 40 relative to the socket 16 and attached telescope tube 12 during operation. A flat plate member 44 is attached to the inner end of the anchor pin 40 so as to extend generally perpendicular to the longitudinal axis of the pin 40. A radial slot 46 is provided in the form of a slot cut in the inner end of the pin 40 with the plate 44 defining the inner wall of the slot 46. The lower corners 47 of the plate 44 may be formed at an angle as shown in FIG. 7 to assist in fitting the plate against the teeth during treatment, as described hereinafter. The anchor pin 40 and the plate 44 may be formed of stainless steel.

As shown in FIGS. 7 and 8, the anchor pin 40 has an axial bore 48 which extends the length of the pin 40. The walls of the bore 48 are threaded as shown so as to receive a threaded screw member 50 through the outer end 52 thereof. The slot 46 extends approximately two-thirds of the distance radially through the pin 40 and the bore 48 is offset from the centerline of the pin 40 sufficiently than the axis of the bore 48 extends to the approximate center of the length of the slot 46. The relationship of the length of the slot 46 to the bore 48 should be such that, with an orthodontic brace wire 54 positioned at the innermost end of the slot 46, the device 10 will be able to slide comfortably on the brace wire 54 with a minimal amount of play.

Figure 10:
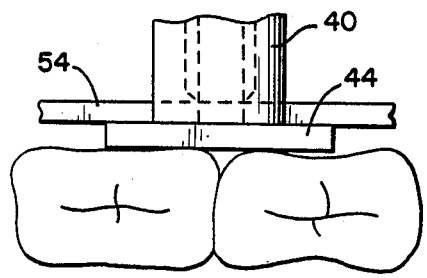
FIG. 10 is a plan view of the inner end of the pin member of FIG. 7 showing the plate attached thereto.

Upon installing the device 10 of FIG. 4 in the mouth of a patient, the anchor pin 40 is mounted on the brace wire 54 as shown in FIGS. 1 and 2. In one method of treatment, the pin 40 is initially positioned so that the pin 40 will slide along the brace wire 54 and abut against a conventional bracket 56 mounted on the teeth for receiving the brace wire 54. In doing so, the plate 44 is preferably positioned as shown in FIG. 10 so that the plate 44 bears against a substantial portion of the vertical surfaces of two adjacent teeth. Thus the force of the spring 30 will be exerted through the anchor pin 40 on the bracket 56 as well as on the plate 44, with the plate 44 exerting force against the adjacent teeth to counteract the tendency of the spring 30 to rotate about its longitudinal axis during opening and closing of the mouth. In this regard, the plate 44 may be made of 300 series soft stainless steel so that the plate 44 may be ground and shaped to fit each individual patient.

On the upper jaw, the lugs 34 of the yoke 20 are passed above and below the upper brace wire 58 and a tie wire 60 is passed through the lug bores 36 interiorly of the brace wire 58 and the ends of the tie wire 60 are then secured together. The enclosure provided by the lugs 34 and the tie wire 60 should be of a size which will enable the device 10 to slide comfortably on the brace wire 58 with a minimal amount of play. In one method of treatment, as shown in FIG. 1, the yoke 20 is initially positioned so that the yoke 20 will slide along the brace wire 58 and abut against a conventional bracket 62 mounted on the teeth. In another method of treatment, as shown in FIG. 2, the tie wire 60 is passed around the brace wire 58 at a position forward of the conventional bracket 64 which itself is forward of the lug 20 position. Thus the tie wire 60 will abut and exert force upon the bracket 64 in this embodiment. In either case, the force of the spring 30 will be exerted on teeth of the upper jaw, in the former case primarily through the yoke 20 and in the latter case primarily through the tie wire 60.

While the embodiment of FIG. 4 is shown in FIGS. 1 and 2 as attached with the anchor pin 40 secured adjacent the lower molars and the yoke 20 secured adjacent the upper incisors and canine teeth, it is also within the scope of the invention to angle the device 10 rearwardly from a point of attachment of pin 40 adjacent the lower incisors and canine teeth so that the yoke 20 is secured adjacent the upper molars.

With regard to the embodiment of FIG. 5, this device 10a can be installed so that the anchor pin 40a will abut against the adjacent forward bracket 70 as shown in FIG. 3. The yoke 20a is installed so that the lugs 34a thereof abut against adjacent rearward bracket 72. Thus the pin 40a and yoke 20a bias the brackets 70, 72 toward the respective telescoping members 12a, 14a. Upon installing the yoke 20a, the innermost lug 34a will pass interiorly of the brace wire 74 as shown in FIG. 3. It will be understood that the device 10a shown in FIGS. 3 and 5 may be employed with as many as two similar devices 10a installed on each side of the mouth, one on the upper and one on the lower jaw.

With regard to spring calibration, the tension is predetermined for each individual unit. Thus the device is made available in different lengths and tensions to take care of different applications, distances between teeth and the like. For example, the device may be constructed so as to exert 4 ounces of force when extended to its maximum dimension. In another application, the device may be constructed so as to exert 6 ounces of force when so extended.

In constructing the present invention, in general it is desirable that adjacent components be formed of stainless steel of different degrees of hardness. Thus, for example, the telescope tube 12 may be formed of hard stainless steel while the telescope plunger 14 is formed of soft stainless steel. The socket 16 and arm 18 may then be formed of soft stainless steel and the anchor pin 40 with ball shaped portion 42 is formed of hard stainless steel. It is advantageous to avoid a construction in which one component of hard stainless steel is connected to an adjacent component which is also of hard stainless steel, thus avoiding a possible galling effect. In one embodiment, hard stainless steel of the 400 series and soft stainless steel of the 300 series were employed.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. An orthodontic device for attachment to teeth of the upper and/or lower jaw of a patient for the purpose of moving teeth with a constant calibrated force, comprising: a telescope mechanism having a telescope outer tube portion and a telescope inner plunger portion; said plunger portion being in the form of a piston rod having an outer end portion bent to form an angle of approximately 45 to 60 degrees with an extension of the remainder of said plunger; attachment means for securing each of the two opposite end portions of said telescope mechanism to at least one tooth of the patient; resilient means in said tube engaging and biasing said telescoping tube portion and plunger portion toward a contracted telescope position with respect to each other; said attachment means comprising, on said outer end portion of said plunger portion, a bifurcated yoke including a pair of lug portions adapted to receive between them an arch wire of orthodontic means affixed to the teeth of said patient, and each lug has a bore therein for receiving a tie wire which, together with said lug portions and the remainder of said yoke, provides an enclosure around said arch wire, and maintains said yoke on said arch wire.

2. An orthodontic device for attachment to teeth of the upper and/or lower jaw of a patient for the purpose of moving teeth with a constant calibrated force, comprising: a telescope mechanism having a telescope outer tube portion and a telescope inner plunger portion; said plunger portion being in the form of a piston rod having an outer end portion bent to form an angle of approximately 45 to 60 degrees with an extension of the remainder of said plunger; attachment means for securing each of the two opposite end portions of said telescope mechanism to at least one tooth of the patient; resilient means in said tube engaging and biasing said telescope tube portion and plunger portion toward a contracted telescoping position with respect to each other; said attachment means comprising, on the opposite end of said tube portion from said plunger end portion, a ball and socket device for attachment to an arch wire of orthodontic means affixed to the teeth of said patient, the socket portion of said ball and socket device being secured to the outer surface of said tube portion, the ball portion of said ball and socket device having a cylindrical anchor pin or trunnion member connected inwardly thereof and a flat plate member attached to the inner end of said cylindrical pin and extending generally perpendicular to the longitudinal axis of said anchor pin, said flat plate member being of sufficient size as to be capable to bearing against a substantial portion of the vertical surfaces of two adjacent teeth in a jaw of said patient.

3. The orthodontic device of claim 2 wherein said anchor pin and said plate member define a radial slot for receiving an arch wire and wherein screw means extends through said ball portion and cylindrical member to said plate member, thus being capable of retaining an arch wire in said slot.

4. The orthodontic device of claim 3 wherein said screw means is positioned off center relative to the longitudinal axis of said cylindrical member so as to extend to the central portion of the length of said radial slot.

5. The orthodontic device of claim 2 wherein said ball and socket member allows said cylindrical member to rotate through an angle of approximately 40 degrees both vertically and laterally.

6. The orthodontic device of claim 2 wherein the socket portion of said ball and socket member is formed in a plane perpendicular to the axis of the socket, which plane extends generally tangentially to said tube portion.

7. The orthodontic device of claim 2 wherein the longitudinal axis of said ball and socket member and said cylindrical member is generally perpendicular to the longitudinal axis of said tube portion.

8. An attachment device for securing orthodontic means to a brace wire on the upper or lower jaw of a patient comprising: a bifurcated yoke secured to said orthodontic means, said bifurcated yoke including a pair of lug portions adapted to receive between them said wire, each lug portion having a bore therein for receiving a tie wire which, together with said lug portions and the remainder of said yoke, provides an enclosure around said brace wire and maintains said yoke mounted on said brace wire, said orthodontic means comprising a telescope mechanism having an outer tube portion and an inner plunger portion and wherein said bifurcated yoke is secured to the outer end of said plunger portion.

9. The attachment device of claim 8 wherein the lug portions of said yoke form an angle of about 110 to 120 degrees with the outer end of said plunger portion to which the yoke is attached.

10. The attachment device of claim 8 wherein the lug portions of said yoke are generally perpendicular to the outer end of said plunger portion to which the yoke is attached.

11. The attachment device of claim 8 wherein said plunger portion is in the form of a piston rod having the outer end portion thereof bent to form an angle of approximately 45 to 60 degrees with an extension of the remainder of said plunger portion, and wherein said lugs are positioned so as to be symmetric with a plane containing the outer end of the plunger portion and passing through said yoke, said bent portion of the plunger portion also lying in said plane.

* * * * *